United States Patent [19]

Amer

[11] Patent Number: 5,248,669

[45] Date of Patent: Sep. 28, 1993

[54] INHIBITION OF ANOXIA OR HYPOXIA-INDUCED, ENDOTHELIUM-MEDIATED VASOSPASM WITH AVERMECTINS

[76] Inventor: Samir Amer, P.O. Box 1439, Santa Barbara, Calif. 93102

[21] Appl. No.: 809,298

[22] Filed: Dec. 17, 1991

[51] Int. Cl.⁵ .............................................. A61K 31/70
[52] U.S. Cl. ........................................ 519/30; 536/7.1
[58] Field of Search ........................... 519/30; 536/7.1

[56] References Cited

U.S. PATENT DOCUMENTS 4,199,569  4/1980  Chabala et al. ..................... 514/30
4,310,519  1/1982  Albers-Schonberg et al. ...... 514/30

Primary Examiner—Johnnie R. Brown
Assistant Examiner—Elli Peselev
Attorney, Agent, or Firm—Samson B. Leavitt; Michael A. Leavitt

[57] ABSTRACT

This invention relates to a method for inhibiting or suppressing in an animal the contraction of vessels lined with endothelial tissue, which contractions are caused by anoxia or hypoxia. The method comprises administering to such an animal an effective therapeutic (contraction-inhibiting) amount of an avermectin class antibiotic such as ivermectin or a derivative thereof for a time period sufficient to inhibit or suppress said contractions.

2 Claims, No Drawings

INHIBITION OF ANOXIA OR HYPOXIA-INDUCED, ENDOTHELIUM-MEDIATED VASOSPASM WITH AVERMECTINS

FIELD OF THE INVENTION

This invention relates to a method for inhibiting or suppressing the release or contracting effect of Endothelium-Derived Contracting Factor (EDCF) caused by anoxia or hypoxia in an animal having an EDCF-releasing endothelium system, which comprises administering to such an animal an effective therapeutic (contraction-inhibiting) amount of an avermectin class antibiotic such as ivermectin or a derivative thereof.

BACKGROUND OF THE INVENTION

Diseases of the circulatory system are a major cause of illness in animals, especially humans, and are responsible for many deaths. In such diseases, decreased tissue oxygenation or ischemia is present. Such decreased tissue oxygenation may be due to a variety of causes. For example, decreased cardiac output can result in decreased perfusion, as can vasoconstriction, partial or complete blockage of blood vessels, leaking or burst blood vessels, decreased oxygenation of the perfusate (as a result of anemia or abnormal hemoglobin), and decreased ability of tissue to extract oxygen. One such disease is atherosclerosis, which is characterized by fatty deposits on the inner surfaces of arteries, which inner surfaces are lined with endothelial cells. These deposits narrow the arteries, resulting in reduced blood flow in such areas of constriction and cause the heart to work harder to drive blood through the circulatory system. In turn, this may lead to a rise in blood pressure. As the blood pressure rises, so does the risk that a blood vessel having a weakness in the wall may rupture, resulting in an aneurism. Other risks relate to the roughness of the artery walls, which may cause blood to clot, thereby causing a blockage where such a clot blocks an arteriole. Or, a piece of the roughened and irregular artery wall may break off and be carried by the blood flow until it reaches an arteriole so narrow that it cannot pass through and thus totally occludes it. If a blockage occurs in the heart, a myocardial infarction or heart attack results. If it occurs in the brain, a stroke results.

In another serious condition, narrowing of coronary arteries due to atherosclerosis may lead to angina or chest pain upon exertion. When the coronary arteries narrow, less blood reaches the heart, and it cannot continue to pump because it needs more oxygen than the narrowed coronary arteries provide. It is this disparity between oxygen supply and demand that results in chest pain (angina) and, possibly, heart attack. Coronary arteries also contract and restrict blood flow in response to a variety of stimuli, one such stimulus being adrenaline or epinephrine, which is released in response to stress. As is well known, when a person faces a stressful situation, adrenaline is released from the adrenal glands and flows into the blood stream and then to the heart. The coronary arteries contract and even less oxygen becomes available to the heart. This may account for those situations which have been reported anecdotally in which people suffer heart attacks when faced with shock or tragic news.

In conditions such as these which result from decreased tissue oxygenation (anoxia, which is defined as the absence or lack of oxygen and is hereafter generically employed to include hypoxia, which is defined as the deficiency or shortage of oxygen), it has been found that such anoxia induces a spasm or contraction in the blood vessels (vasospasm) supplying the anoxic tissue. These spasms have the effect of further reducing the blood supply to the tissue in question thereby further aggravating the effects of the lack of tissue oxygenation. Frequently, this results in irreversible damage to certain tissue, such as heart tissue, which cannot be revived after its death. This process of secondary vasospasm, or further contraction of the arteries and even further restriction of blood flow, is mediated by the endothelium, which releases a material that has been identified as Endothelium-Derived Contracting Factor or EDCF.

OBJECTS OF THE INVENTION

It is, accordingly, an object of this invention to provide a method of suppressing or inhibiting the release (which also or alternatively includes inhibiting the contracting effect) of Endothelium-Derived Contracting Factor (EDCF) caused by anoxia in an animal (including humans) having an EDCF-releasing endothelium system.

Another object of this invention is to provide a method of inhibiting or suppressing in an animal the contraction of cerebrovascular vessels lined with endothelial tissue.

A further object of this invention is to provide a method for inhibiting or suppressing in an animal the contraction of coronary arteries lined with endothelial tissue.

It is yet another object of this invention to provide a prophylactic treatment method for the prevention of ischemic episodes and recurrent pain in animals, especially human patients prone to suffering from angina, which angina is exacerbated by the release of Endothelium-Derived Contracting Factor (EDCF) caused by anoxia or hypoxia in an animal having an EDCF-releasing endothelium system.

Other objects and advantages will appear as the description proceeds.

SUMMARY OF THE INVENTION

The attainment of one or more of such objects is made possible by this invention which relates to a method and a new use for a class of pharmaceutical agents, previously known for other purposes, for suppressing or inhibiting the release or contraction effect of Endothelium-Derived Contracting Factor (EDCF) caused by anoxia in an animal having an EDCF-releasing endothelium system. The method involves administering to a susceptible animal an avermectin class antibiotic at an effective dose which does not cause undesirable side effects. A preferred antibiotic is ivermectin. These substances may be administered in admixture with a pharmaceutically acceptable carrier. In in vitro lab tests, an avermectin agent of this invention was shown to reduce or block entirely the release or contracting effect of EDCF from the endothelium. Thus, when the coronary arteries contracted and restricted blood flow, no EDCF was released or its effect nullified and no further restriction of blood flow occurred. This method, therefore, and these agents should help the heart tissue to recover sooner and suffer less irreparable damage when coronary arteries contract and restrict blood flow thereto. Illustrative dosages especially for humans may range from about 0.0010 to about 10 mg.

per kg. of body weight taken from about three times per day to once a year.

DETAILED DESCRIPTION OF THE INVENTION

This invention relates to a new use for a known class of pharmaceutical agents which may be administered to an animal, including mammals in general and humans in particular, having an endothelium system capable of releasing Endothelium-Derived Contracting Factor (EDCF) in response to anoxia. These agents comprise the avermectin antibiotics, including ivermectin and derivatives thereof, and they may be administered in admixture with a pharmaceutically acceptable carrier.

As described in the Merck Index and the literature references cited therein, the avermectins comprise a class of broad spectrum antiparasitic antibiotics which are derivatives of pentacyclic 16-membered lactones related to the milbemycins. They are further described in U.S. Pat. No. 4,310,519, and German patent 2,717,040 which are assigned to Merck & Co. and are incorporated herein by reference. They are described generically as C-076 compounds, and there are eight different C-076 compounds, which are given the designations A1a, A1b, A2a, A2b, B1a, B1b, B2a, B2b based upon the structure of the individual compounds.

As described in U.S. Pat. No. 4,310,519, the avermectin antibiotics have the following formula:

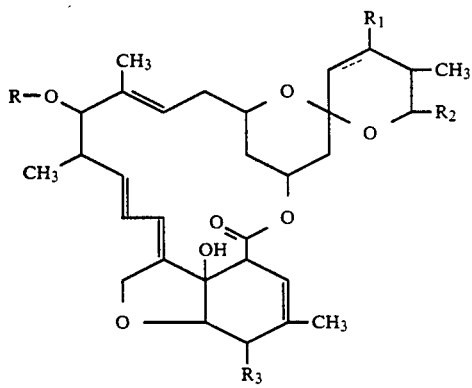

wherein R is:

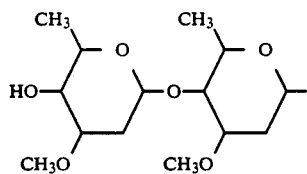

and wherein the broken line indicates a single or double bond; $R_1$ is hydroxy and is present only when the broken line indicates a single bond; $R_2$ is isopropyl or sec-butyl; and $R_3$ is methoxy or hydroxy.

In the foregoing structural formula, the individual C-076 compounds are as set forth below:

|  | $R_1$ | $R_2$ | $R_3$ |
|---|---|---|---|
| A1a | Double bond | sec-butyl | —OCH$_3$ |
| A1b | Double bond | iso-propyl | —OCH$_3$ |
| A2a | —OH | sec-butyl | —OCH$_3$ |
| A2b | —OH | iso-propyl | —OCH$_3$ |
| B1a | Double bond | sec-butyl | —OH |

-continued

|  | $R_1$ | $R_2$ | $R_3$ |
|---|---|---|---|
| B1b | Double bond | iso-propyl | —OH |
| B2a | —OH | sec-butyl | —OH |
| B2b | —OH | iso-propyl | —OH |

Other derivatives of avermectin and milbemycin are disclosed in U.S. Pat. No. 5,055,596, which is assigned to the Beecham Group p.l.c. and is incorporated herein by reference thereto. According to the patent, the prior art and inventive compounds disclosed therein have parasiticidal properties and are said to provide a method of treatment or prophylaxis of endo- and ectoparasitic infestations, especially helminthiasis, of animals, especially humans. Such compounds are effective in the present inventive process of treatment Suitable formulations thereof may be administered orally, parenterally, percutaneously, as a food additive, or may be prepared as an aerosol spray formulation. One type of such compound has the following formula:

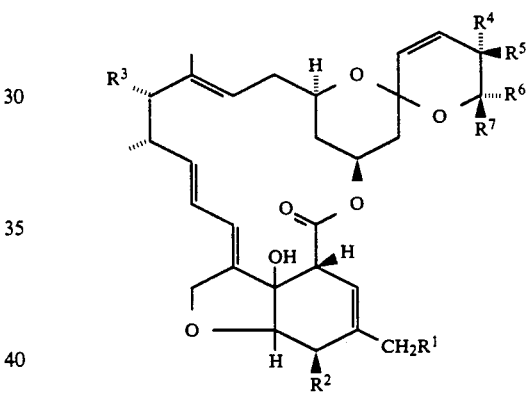

wherein $R^1$ is hydrogen or optionally protected hydroxy; $R^2$ is alkoxy, optionally protected hydroxy, oxo or optionally O-substituted oximino; $R^3$ is hydrogen, optionally protected hydroxy, or one of a group of 4'-(a-L-oleondrosyl)-a-L-oleandrosyloxy or a-L-oleandrosyloxy wherein the terminal hydroxy group is optionally protected; one of $R^4$ and $R^5$ is hydrogen and the other is methyl; and one of $R^6$ and $R^7$ is hydrogen and the other is methyl; with the proviso that (a) when $R^1$ is optionally protected hydroxy, $R^3$ is hydrogen, and (b) when $R^2$ is not methoxy or optionally protected hydroxy, $R^1$ and $R^3$ are both hydrogen.

As also described in the Merck Index and the references cited therein, ivermectin is a semi-synthetic derivative of abamectin, one of the avermectins. It contains at least 80% of 22,23 dihydroavermectin B1a and not more than 20% of 22,23 dihydroavermectin B1b. Its preparation is described in Japanese Kokai 79 61198 and U.S. Pat. No. 4,199,569 to Chabala et al, which are incorporated herein by reference.

As described in U.S. Pat. No. 4,199,569, ivermectin has the following formula:

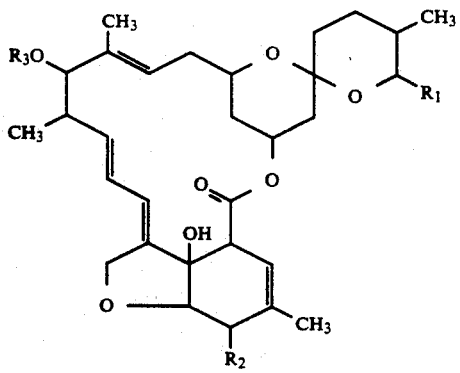

wherein $R_1$ is iso-propyl or sec butyl; $R_2$ is methoxy, hydroxy or loweralkanoyloxy; and $R_3$ is hydrogen, loweralkanoyl, a-L-oleandrosyl, 4'-loweralkanoyl-a-L-oleandrosyl, 4'-(a-L-oleandrosyl)-a-L-oleandrosyl, or 4''-loweralkanoyl-4'-(a-L-oleandrosyl)-a-L-oleandrosyl.

In the foregoing structural formula, the individual C-076 compounds are as set forth below:

|     | $R_1$       | $R_2$      | $R_3$   |
|-----|-------------|------------|---------|
| A1a | Double bond | sec-butyl  | —$OCH_3$ |
| A1b | Double bond | iso-propyl | —$OCH_3$ |
| A2a | —OH         | sec-butyl  | —$OCH_3$ |
| A2b | —OH         | iso-propyl | —$OCH_3$ |
| B1a | Double bond | sec-butyl  | —OH     |
| B1b | Double bond | iso-propyl | —OH     |
| B2a | —OH         | sec-butyl  | —OH     |
| B2b | —OH         | iso-propyl | —OH     |

Ivermectin is available from Merck & Co. under the trade name Mectizan and has broad anti-parasitic activity. It is used primarily in veterinary medicine for the treatment of nematodes in sheep, cows and other domestic animals. In the laboratory, it is used for the treatment of heart worms in dogs. Recently, and as described further below, it has been used successfully to treat river blindness in man.

In a series of experiments conducted at the Baylor College of Medicine, Houston, Tex., using aortic rings from dogs, ivermectin was found to produce highly surprising results. In baths normally oxygenated, aortic rings from dogs previously treated with ivermectin failed to contract in response to anoxia induced by replacing the oxygen in the bath with nitrogen, in contrast to contractions in dog rings not previously treated with ivermectin. These experimental results establish that ivermectin inhibits or suppresses endothelium-mediated contractions normally induced by anoxia or hypoxia.

The aforesaid series of experiments were conducted as follows. Normal dogs were divided into two groups: one group received ivermectin 10 mg/kg by mouth and the second or control group received none. Two weeks later, the dogs were killed and their coronary arteries removed and tested in vitro. Blood vessels from both an ivermectin-treated dog and an untreated dog were studied in parallel. The coronary arteries were cut into rings and their contractions in response to Prostaglandin F-2alpha (PGF-2alpha), a substitute for adrenaline, were measured. After the contractions reached a plateau, nitrogen was bubbled into bath fluid bathing the coronary arterial rings to simulate anoxia or hypoxia. Normally, a mixture of 95% oxygen and 5% carbon dioxide would be bubbled into such a bath fluid.

In the control tissues, the addition of nitrogen caused substantial further contractions because the anoxia caused the release from the endothelium of EDCF which mediated the observed additional contractions. However, in the dogs previously treated with ivermectin, no additional contractions in response to the same nitrogen-induced anoxia occurred. These results establish that ivermectin inhibits or suppresses the release or contracting effect of EDCF from the endothelium and prevents further contractions.

In another series of experiments conducted at the Baylor College of Medicine, using the methodology outlined above, sections of coronary arteries obtained from dogs treated with ivermectin but with the endothelium removed reacted to PGF-2alpha and nitrogen in substantially the same manner as those also treated with ivermectin but with the endothelium intact. As shown in Table A below, in the presence of ivermectin (IVM), no substantial difference in contractions (as measured in grams of tension) is seen between the rings having intact endothelial tissue (column III) and those having their endothelial tissue removed (column IV).

More particularly, in dogs with the endothelium removed, no EDCF could be released to produce further contractions. In dogs with the endothelium intact, the release or contracting effect of the EDCF from the endothelium was inhibited by the ivermectin, hence, also no additional contractions.

Columns I and II in Table A show that in the same series of experiments, coronary artery rings from non-ivermectin-treated, saline-treated control dogs with intact endothelia (column I) exhibited contractions (average 13) due to uninhibited release of EDCF from the endothelium over 3 times greater than the contractions (average 3.88) of similar control dog rings with endothelium removed (column II) i.e., with no source of EDCF.

TABLE A

| Anoxia Induced Contractions in Dog Coronary Artery Rings* | | | |
|---|---|---|---|
| Saline Control Dogs | | IVM-Treated Dogs | |
| I. Endothelium Present | II. Endothelium Absent | III. Endothelium Present | IV. Endothelium Absent |
| 13 ± 2.29[17] | 3.88 ± 1.31[16] | 4.06 ± 1.44[16] | 3.06 ± 1.77[16] |

(*In grams of tension ± Standard Deviation; number in brackets is the number of experiments.)

The importance of these findings is apparent. In conditions that result from decreased tissue oxygenation (anoxia or hypoxia), as, for example, heart attacks and strokes, the anoxia or hypoxia induces a secondary spasm or contraction in the blood vessels supplying the anoxic or hypoxic tissue. This secondary spasm further reduces the blood supply to the tissue in question and aggravates the effects of the lack of oxygenation and frequently results in irreversible damage to the tissues. Ivermectin, by virtue of its ability to inhibit the anoxia or hypoxia-induced secondary vasospasm (which is primarily endothelium-mediated), can significantly reduce the serious side-effects and tissue damage resulting from ischemia.

These results are considered applicable to humans, since the EDCF-releasing endothelium system in dogs is identical to that in man. This conclusion is supported by the fact that ivermectin has been found to be effective and well tolerated in humans in the treatment of river blindness and parasites.

As reported in the literature, ivermectin has been used successfully to treat internal and skin parasites and river blindness in man. Several such articles, all of which cite additional articles on the use of ivermectin in human and animal medicine, include the following:

(1) Richards Jr. et al, "Comparison of High Dose Ivermectin and Diethylycarbamazine for Activity Against Bancroftian Filariasis in Haiti," *American Journal of Tropical Medical Hygiene*, Vol. 44, No. 1 pp 3–10 (90–221), (1991).

(2) Pacque et al, "Improvement in Severe Onchocercal Skin Disease After a Single Dose of Ivermectin," *The American Journal of Medicine*, Vol. 90, pp. 590–594, (1991).

(3) Duke et al, "Migration and Death of Skin-Dwelling Onchocerca Volvulus Microfilariae After Treatment with Ivermectin," *Trop. Med. Parasitol*, Vol 42, pp. 25–30, (1991).

(4) Cook, "Anthelminthic Agents: Some Recent Developments and Their Clinical Application," *Postgraduate Medical Journal*, Vol. 67, pp. 16–22, (1991).

(5) Dadzie et al, "Onchocerciasis Control By Large-Scale Ivermectin Treatment," *The Lancet*, Vol. 337, pp. 1358–1359, (991).

The dosages reported are as follows; Richards Jr. —1 single 1 mg oral dose, followed by a single oral dose of 200 mcg/kg of body weight for one group and 200 mcg/kg per day for two days for a second group; Pacque et al—single annual dose 150 mcg/kg; Duke et al—122–200 mcg/kg (as a single 6 mg Mectizan tablet); and Cook—100–200 mcg/kg which lasted for 6–12 months.

The following examples are only illustrative of preferred embodiments of the invention and are not to be regarded as limitative. As employed herein and in the appended claims, all amounts and proportions are by weight and temperatures are in degrees F unless otherwise indicated.

EXAMPLE I

Tablet Formulation

Since an average man weighs about 70 kg, tablets containing about 10 mg ivermectin (e.g. about 150 mcg or 0.15 mg/kg body weight) is recommended having the following illustrative formulation:

| Ingredient | In each | in 10,000 |
|---|---|---|
| Ivermectin | 10.0 mg | 100 gm |
| Microcrystalline cellulose | 15.9 mg | 159 gm |
| Stearic acid | 0.9 mg | 9 gm |
| Colloidal silica | 0.2 mg | 2 gm |
| Total | 27.0 mg | 270 gm |

All ingredients are blended in a suitable blender. The tablets are prepared by compression in a suitable standard concave punch. Ten tablets weigh 270 mg. One tablet is taken every day, week, alternate week, month, semi-annually, or annually depending on the weight, age, gender, condition, etc. of the human patient or consumer, to inhibit the release or contracting effect of EDCF caused by anoxia or hypoxia.

EXAMPLE II

Another example of a suitable tablet is as follows:

| Ingredient | In each | In 10,000 |
|---|---|---|
| Ivermectin | 10.0 mg | 100 gm |
| Compressible Starch | 10.0 mg | 100 gm |
| Stearic acid | 1.0 mg | 10 gm |
| Silica gel | 0.3 mg | 3 gm |
| Total | 21.3 mg | 213 gm |

All ingredients are blended in a twin shell blender for 15 minutes and then compressed in a standard concave punch. Ten tablets weigh 213 mg. The tablets are taken as in Example I with similar effect.

In these Examples, the cellulose (in Example I) and the starch (in Example II) act as a diluent to increase the bulk and weight of the tablets to a size and amount convenient for manufacturing and as a binder to keep the material to be compressed into a tablet in granular form and to hold the tablet together. The stearic acid acts as an anti-adhesive or anti-sticking agent or lubricant to improve the flow rate of the granulated material, to prevent adhesion of the tablet material to the surfaces of the tablet die and punches, and to reduce interparticle friction and facilitate ejection of the tablet from the die cavity. The silica acts as a drying agent or dessicant. In addition to these processing aids, tablets may also contain flavorings and disintegrators, which act to facilitate their break-up or disintegration after administration.

EXAMPLE III

Injectable Formulation

| Invermectin | 100.0 mg |
|---|---|
| Sodium Bisulfate | 26.00 mg |
| Sodium Citrate | 10.00 mg |
| Water for Injection up to | 20.00 ml |

The ingredients are mixed under aseptic conditions until dissolved and are then filtered and sterilized by passage through a bacterial filter in an aseptic area. Sodium bisulfite acts as an antioxidant enhances the stability of the product. Sodium citrate is present to increase the molality and act as a buffer. Other materials may be added to parenteral solutions to make them isotonic, to buffer them, to adjust the pH, or to act as local anesthetic agents. Bacteriostatic agents or preservatives may be necessary additives in multiple dose containers of parenteral solutions. The final concentration is 5 mg ivermectin per ml of solution for injection, as needed to inhibit the release or contracting effect of EDCF caused by anoxia or hypoxia.

As a prophylactic treatment for heart attacks and strokes in susceptible populations, susceptible individuals, with angina for example, should be treated with ivermectin to help prevent ischemic episodes and recurrent pain. Moreover, anoxia and hypoxia do not occur only in the heart; they can occur in the extremities as well as in any other susceptible, endothelial-lined tissue. Ivermectin, therefore, may prevent secondary vasospasms such as, cerebrovasospasms, whenever anoxia or hypoxia is suspected.

Ivermectin may be taken orally, in powder, tablet or capsule form for example; parenterally by intravenous, subcutaneous, or intramuscular injection; topically; rectally; or by inhalation therapy. A suitable dose would range between 0.001–10 mg/kg, preferably about 50 to 300 mcg/kg, body weight and would be repeated as needed.

The compositions of this invention may be prepared and used in any suitable solid or liquid form, e.g. powder, paste, tablet, lozenge, gel, chewing gum, solution, suspension, emulsion, aerosol or the like. These compositions may contain avermectin in amounts ranging from less than 1% to over 99%, with the remainder being a pharmaceutically acceptable solid or liquid carrier, which may contain other conventional excipients. Examples of such carriers and excipients include fillers, binders, flavors, sweeteners, bulking and coloring agents, antioxidants, anionic, nonionic, cationic, zwitterionic, and amphoteric surface active detergents, sudsing, dispersing and emulsifying agents, buffering and pH adjusting agents, water and organic solvents, humectants, thickeners, preservatives, stabilizers, mold release agents, disintegrants, anti-disintegrants, lubricants and the like. Examples of conventional pharmaceutically acceptable carriers and excipients are profusely disclosed in the prior art including discussions in U.S. Pat. No. 4,515,772 (Parran et al, Proctor & Gamble), U.S. Pat. No. 4,966,777 (Gaffar et al, Colgate-Palmolive Company), and U.S. Pat. No. 4,728,512 (Mehta et al, American Home Products), which discussions are incorporated herein by reference thereto.

Generally speaking, this invention is directed to a method for inhibiting or suppressing in an animal or human body the contraction of vessels lined with endothelial tissue, which contractions are caused by anoxia or hypoxia. The method comprises administering to such an animal or human, especially mammals, an effective therapeutic amount of an avermectin compound or antibiotic such as ivermectin or a derivative thereof. It is further directed to a method of inhibiting or suppressing the release or contracting effect of Endothelium-Derived Contracting Factor (EDCF) caused by anoxia or hypoxia in an animal having an EDCF releasing endothelium system, which comprises administering to such an animal an effective therapeutic (contraction inhibiting) amount of an avermectin family antibiotic such as ivermectin or a derivative thereof.

It will be understood that the foregoing discussion, as completed by the specific examples, only illustrates the invention and its principles. However, many modifications and variations in the details of the disclosure will occur to those skilled in the art to which this invention relates and still remain within the scope and principles of the invention. For example, the illustrative embodiments of the invention deal primarily with the material ivermectin. It is apparent, however, that the principles of the invention can be applied or other avermectins as well as derivatives of ivermectin, such as those disclosed in U.S. Pat. No. 4,199,569. In general, this invention includes a prophylactic method for treating angina-prone animals, which angina is exacerbated by the contraction of coronary arteries lined with endothelial tissue in response to anoxia or hypoxia, which method comprises administering to such a susceptible animal an effective therapeutic (contraction inhibiting) amount of an avermectin antibiotic such as ivermectin or an analog or derivative thereof.

This invention has been disclosed with respect to preferred embodiments, and it will be understood that variations and modifications thereof obvious to those skilled in the art are intended to be included within the spirit and purview of this application and the scope of the appended claims.

What is claimed is:

1. A method for inhibiting secondary contractions in endothelium-lined blood vessels of a mammal undergoing anoxia which induces such contractions comprising administering to such mammal ivermectin antibiotic in an effective contraction-inhibiting dosage amount ranging from about 0.0010 to 10 mg/kg body weight about three times per day to once year.

2. The method of claim 1 where said antibiotic is administered by a method selected from the group consisting of intravenous injection, intramuscular injection, subcutaneous injection, oral administration, topical administration, rectal administration, and inhalation therapy.

* * * * *